United States Patent
Shiino et al.

(10) Patent No.: US 6,214,957 B1
(45) Date of Patent: Apr. 10, 2001

(54) SOLUBILIZERS, EMULSIFIERS AND DISPERSANTS

(75) Inventors: Daijiro Shiino; Kazunori Waki, both of Tsukuba; Nobuo Nakabayashi, 6-20, Koganehara 5-chome, Matsudo-shi, Chiba 270; Kazuhiko Ishihara, 3-16-37, Josuihoncho, Kodaira-shi, Tokyo 187, all of (JP)

(73) Assignees: NOF Corporation, Tokyo; Japan Science Technology Corporation, Saitama; Nobuo Nakabayashi, Chiba; Kazuhiko Ishihara, Tokyo, all of (JP)

( * ) Notice: Subject to any disclaimer, the term of this patent is extended or adjusted under 35 U.S.C. 154(b) by 0 days.

(21) Appl. No.: 09/230,828

(22) PCT Filed: Jul. 30, 1997

(86) PCT No.: PCT/JP97/02644

§ 371 Date: Jan. 29, 1999

§ 102(e) Date: Jan. 29, 1999

(87) PCT Pub. No.: WO98/04341

PCT Pub. Date: Feb. 5, 1998

(30) Foreign Application Priority Data

Jul. 31, 1996 (JP) .................................................. 8-202620
Jul. 30, 1997 (JP) .................................................. 9-204656

(51) Int. Cl.$^7$ ................................................. C08F 230/02
(52) U.S. Cl. .................... 526/278; 526/274; 526/277; 526/310; 526/312; 526/328; 526/328.5
(58) Field of Search .................... 526/274, 277, 526/278, 310, 312, 328, 328.5

(56) References Cited

FOREIGN PATENT DOCUMENTS

| | | |
|---|---|---|
| 2-172529 | 7/1990 | (JP) . |
| 3-76762 | 4/1991 | (JP) . |
| 6-41157 | 2/1994 | (JP) . |
| 7-68147 | 3/1995 | (JP) . |
| 3-64373 | 12/1996 | (JP) . |
| 94/14897 | * 7/1994 | (WO) . |

OTHER PUBLICATIONS

Ishihara et al., Biomaterials, 16 (Jul. 1996), 873–879.*

Sugiyama et al., Macromol. Chem. Phys., 196, 1907–1916 (Jul. 1995).*

* cited by examiner

*Primary Examiner*—Helen L. Pezzzuto
(74) *Attorney, Agent, or Firm*—Darby & Darby

(57) ABSTRACT

Solubilizers, emulsifiers and dispersing agents having the effects of moisturizing the skin when used as washing agents and having the character of elevating the concentration of a material to be solubilized, emulsified or dispersed in solvents including water as compared with the case where the material is employed alone, or elevating the apparent concentration of a material to be emulsified or dispersed in solvents by increasing homogeneity of the emulsion or dispersion which contain as the active ingredient polymers obtained by polymerizing monomer compositions containing at least one hydrophilic monomer (a) having a group represented by general formula (1) in the side chain, wherein $R^1$, $R^2$ and $R^3$ represent each H or C1–4 alkyl.

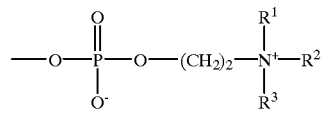

(1)

9 Claims, 1 Drawing Sheet

SOLUBILIZERS, EMULSIFIERS AND DISPERSANTS

FIELD OF ART

The present invention relates to solubilizers, emulsifiers and dispersing agents having a function of solubilizing, emulsifying or dispersing various compounds or materials, and which can be used in the fields of washing agents, coatings, chemical products, and pharmaceuticals.

BACKGROUND OF ART

In various fields of art, various surfactants are widely used as washing agents, solubilizers, emulsifiers and dispersing agents. Substances to be solubilized, emulsified or dispersed may include dirt to be washed off, as well as oils and fats, agents and chemical products in the field of pharmaceuticals.

As high-molecular surfactants has been known polyoxyethylene monostearate, polyoxyethylene monooleate, polyoxyethylene sorbitan monooleate, polyoxyethylene sorbitan trioleate, polyoxyethylene monolauryl ether, polyvinyl pyrrolidone, carboxymethyl cellulose, hydroxypropyl cellulose, gelatine and gum arabic. However, when such high-molecular surfactants are used as a skin washing agent, these surfactants cannot always give a good effect on skin. Particularly, such surfactants cannot give a moistness feeling on skin.

In the pharmaceutical field, the various high-molecular surfactants are known to be useful as a suspending agent or an emulsifying agent (Japanese Pharmacopoeia, 13th edition, Hirokawa Shoten, Tokyo, 1996).

Further, it is known that albumin, gelatine, starch or agarose, which are surfactants derived from natural organisms, can be used as a drug carrier for improving apparent solubility of a drug (Iyakuhin no Kaihatsu (development of pharmaceuticals), 13th edition, Yakubutsu-soutatsuhou (drug derivery), edited by Hitoshi SEZAKI, Torakawa Shoten (1995), p216–331). It is also known that a block copolymer of polyethylene glycol-poly amino acid, a surfactant not derived from natural organisms, can be used as a drug carrier (Japanese Laid-open Patent Application No.1994-107565).

The safety of the above-mentioned surfactants derived from natural organisms is lowered by contamination. The surfactants not derived from natural organisms do not exhibit sufficient solubilizing, emulsifying or dispersing ability depending on the nature of substances to be solubilized, emulsified or dispersed.

It is known that a homopolymer of 2-methacryloyloxyethyl phosphorylcholine and a copolymer of 2-methacryloyloxyethyl phosphorylcholine and hydrophilic and/or hydrophobic monomers exhibit moisture retaining effect and anti-chapping effect on skin, and can be used for cosmetics (Japanese Laid-open Patent Application Nos.93-70321, 94-157269, 94-157270 and 94-157271). However, it is not known that these polymers exhibit solubilizing, emulsifying and dispersing effect.

DISCLOSURE OF THE INVENTION

The object of the present invention is to provide a solubilizer, an emulsifier, or a dispersing agent that can give moistness feeling to the skin when used as a skin washing agent. Another object of the present invention is to provide a solubilizer, an emulsifier or a dispersing agent having the character of elevating the concentration of a material to be solubilized, emulsified or dispersed in solvents including water as compared with the case where the material is employed alone, or elevating the apparent concentration of a material to be emulsified or dispersed in solvents by increasing homogeneity of the emulsion or dispersion.

The present inventors made extensive studies in the light of the above problems, and found out that a polymer of a hydrophilic monomer, and a polymer produced by polymerizing a monomer composition containing a specific hydrophilic monomer and hydrophobic monomer, can be an excellent solubilizer, emulsifier and dispersing agent, to accomplish the present invention.

That is, according to the present invention, there is provided a solubilizer, an emulsifier or a dispersing agent comprising as an effective ingredient a polymer produced by polymerizing a monomer composition containing a hydrophilic monomer (a) having in a side chain thereof a group represented by the formula (1):

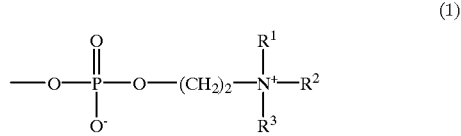

(1)

wherein $R^1$, $R^2$ and $R^3$ denote a hydrogen atom or an alkyl group having 1 to 4 carbon atoms, and are the same or different groups.

According to the present invention, there is further provided a solubilizer, an emulsifier or a dispersing agent comprising as an effective ingredient a polymer produced by polymerizing a monomer composition consisting of, as a hydrophilic monomer (a), 100 to 20 wt % of 2-(methacryloyloxy)ethyl-2'-(alkyl-substituted or non-substituted ammonio)ethyl phosphate represented by the formula (2):

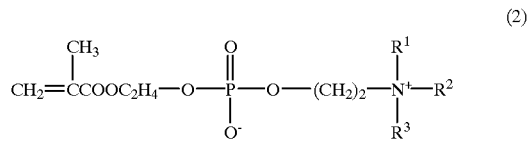

(2)

(wherein $R^1$, $R^2$ and $R^3$ denote a hydrogen atom or an alkyl group having 1 to 4 carbon atoms, and are the same or different groups) and, as a hydrophobic monomer (b), 0 to 80 wt % of (meth)acrylate represented by the formula (3):

(3)

(wherein $R^4$ denotes a hydrogen atom or a methyl group, and $R^5$ denotes an alkyl group having 4 to 8 carbon atoms).

PREFERRED EMBODIMENTS OF THE INVENTION

Figure 1:
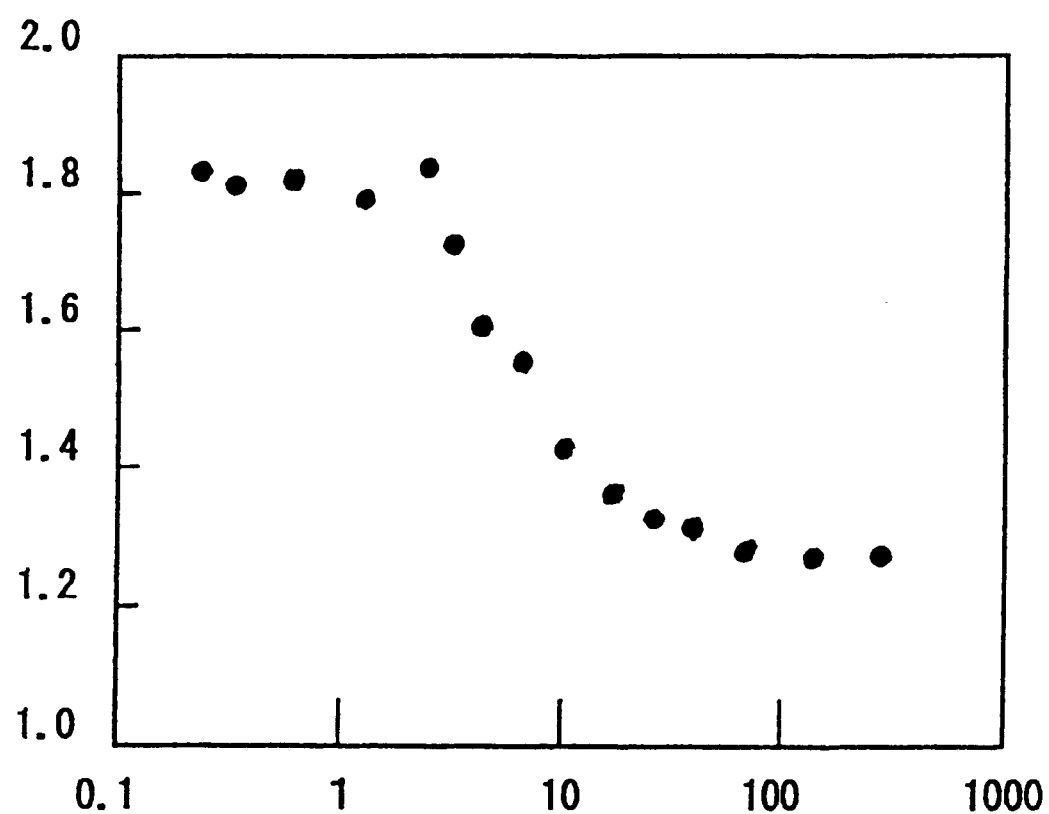
FIG. 1 is a graph showing the measurement of critical micelle concentration of polymer A performed in the Referential Example 1.

In the present invention, solubilizing means obtaining a transparent or semitransparent homogenous solution when a substance to be solubilized is dissolved in a solvent. In the present invention, emulsifying means obtaining a homogenous emulsion when a substance to be emulsified is dispersed when a liquid substance and a solvent are emulsified. In the present invention, dispersing means obtaining a homogenous dispersion when a solid substance is dispersed in a solvent.

The present solubilizer, emulsifier or dispersing agent is an agent that improves solubility, emulsifying capacity or dispersion capacity of a solvent, compared to the inherent capacity of the solvent in which materials such as resin or drugs are dissolved, emulsified or dispersed alone. The present solubilizer, emulsifier or dispersing agent contains as an effective ingredient a polymer produced by polymerizing a monomer composition containing the hydrophilic monomer (a) having the group represented by the above formula (1), and optionally the hydrophobic monomer (b).

In the monomer composition, which is a starting material for the present solubilizer, emulsifier and dispersing agent, the hydrophilic monomer (a) having the group represented by the formula (1) in the side chain thereof may preferably be monomers having a polymerizable double bond in the molecule and having the group represented by the formula (1) in the side chain thereof.

The examples of the hydrophilic monomer (a) may include 2-(meth)acryloyloxyethyl-2'-(trimethylammonio)ethyl phosphate, 3-(meth)acryloyloxypropyl-2'-(trimethylammonio)ethyl phosphate, 4-(meth)acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(triethylammonio)ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(vinyloxy)ethyl-2'-(trimethylammonio)ethyl phosphate, 2-(allyloxy)ethyl-2'-(trimethylammonio)ethyl phosphate, 2-(p-vinylbenzyloxy)ethyl-2'-(trimethylammonio)ethyl phosphate, 2-(p-vinylbenzoyloxy)ethyl-2'-(trimethylammonio)ethyl phosphate, 2-(styryloxy)ethyl-2'-(trimethylammonio)ethyl phosphate, 2-(p-vinylbenzyl)ethyl-2'-(trimethylammonio)ethyl phosphate, 2-(vinyloxycarbonyl)ethyl-2'-(trimethylammonio)ethyl phosphate, 2-(allyloxycarbonyl)ethyl-2'-(trimethylammonio)ethyl phosphate, 2-(acryloylamino)ethyl-2'-(trimethylammonio)ethyl phosphate, 2-(vinylcarbonylamino)ethyl-2'-(trimethylammonio)ethyl phosphate, 2-(allyloxycarbonylamino)ethyl-2'-(trimethylanmmonio)ethyl phosphate, 2-(butenyloxy)ethyl-2'-(trimethylammonio)ethyl phosphate, 2-(crotonoyloxy)ethyl-2'-(trimethylammonio)ethyl phosphate, ethyl-(2'-trimethylammonioethylphosphorylethyl)fumarate, butyl-(2'-trimethylammonioethylphosphorylethyl)fumartate, hydroxyethyl-(2'-trimethylammonioethylphosphorylethyl)fumarate, ethyl-(2'-trimethylammonioethylphosphorylethyl)fumarate, butyl-(2'-trimethylammonioethylphosphorylethyl)fumarate, and hydroxyethyl-(2'-trimethylammonioethylphosphorylethyl)fumarate. In terms of availability, the compounds represented by the above formula (2) are preferable. Particularly 2-(methacryoyloxy)ethyl-2'-(trimethylammonio)ethyl phosphate (that is, 2-methacryloyloxyethyl phosphorylcholine, abbreviated hereinbelow as "MPC") is preferable. These compounds may be used solely or as mixtures.

The monomer composition, which is the starting material for the present solubilizer, emulsifier or dispersing agent, may optionally contain the hydrophobic monomer (b). The examples of the hydrophobic monomer (b) may include, e.g., (meth)acrylic acid, aconitic acid, itaconic acid, mesaconic acid, citraconic acid, fumaric acid, maleic acid, vinylsulfonic acid, acrylamide-2-methylpropanesulfonic acid, vinylsulfonic acid, and metal salts thereof; N,N-dimehylaminopropyl (meth)acrylamide, N,N-dimethylaminoethyl (meth)acrylate, N,N-diethylaminoethyl (meth)acrylate, and quaternary salts thereof; 2-vinylpyridine, 3-vinylpyridine, 4-vinylpyridine, 2-vinylimidazole, N-methyl-2-vinylimidazole, N-vinylimidazole, (meth)acrylamide, N-methyl(meth)acrylamide, N,N-dimethyl(meth)acrylamide, N-ethyl(meth)acrylamide, N-isopropyl(meth)acrylamide, N-t-butyl(meth)acrylamide, 2-hydroxyethyl (meth)acrylate, (meth)acrylic acid monoglycerol, N-(tris(hydroxymethyl)methyl)acrylamide, vinyl methyl ether, polyethylene glycol (meth)acrylate, N-vinylpyrrolidone, N-(meth)acryloylpyrrolidone, acryloyl morpholine, maleimide, vinyl acetate, and maleic anhydride; styrene monomers such as styrene, methylstyrene, chloromethylstyrene, and aminostyrene; various monoalkyl (meth)acrylates such as methyl (meth)acrylate, ethyl (meth)acrylate, butyl (meth)acrylate, dodecyl (meth)acrylate, cetyl (meth)acrylate, stearyl (meth)acrylate, cyclohexyl (meth)acrylate and 2-ethylhexyl (meth)acrylate; (meth)acrylates containing a reactive functional group such as glycidyl (meth)acrylate and (meth)acryloyloxyethyl trimethoxysilane; denatuated urethane (meth)acrylates such as 2-(meth)acryloyloxyethyl butyl urethane, 2-(meth)acryloyloxyethyl benzyl urethane, and 2-(meth)acryloyloxyethyl phenyl urethane; ethyl vinyl ether, butyl vinyl ether, vinyl acetate, vinyl chloride, vinylidene chloride, ethylene, propylene, isobutylene, diethyl fumarate, diethyl maleate, acrylonitrile and vinylbenzylamine. Among these, the hydrophobic monomer (b) represented by the above formula (3) is particularly preferred.

As the combination of the hydrophilic monomer (a) and the hydrophobic monomer (b), a combination of butyl methacrylate or 2-ethylhexylmethacrylate and the MPC is the most preferable. If vinyl acetate, maleic anhydride or glycidyl (meth)acrylate is additionally employed as a comonomer, hydrolysis or ring opening for giving hydrophilicity may be performed after polymerization, to further improve hydrophilicity. Alternatively, if glycidyl (meth)acrylate or (meth)acryloyloxyethyltrimethoxysilane is employed, a reaction for giving hydrophobicity may be performed after polymerization, to improve hydrophobicity.

The preferable content of the hydrophilic monomer (a) in the monomer composition is 100 to 20 wt %, and particularly 100 to 30 wt % of the total unsaturated monomers in the monomer composition. If the content is less than 20 wt %, solubility of the resulting polymer in water is lowered, thus not being preferable. The content of the hydrophobic polymer (b) in the monomer composition is preferably in a range of 0 to 80 wt %, and particularly 0 to 70 wt % of the total unsaturated monomers in the monomer composition. If the content is more than 80 wt %, solubility of the resulting polymer in water is lowered, thus not being preferable.

The effective ingredient of the present solubilizer is the polymer produced by polymerizing the monomer composition. The weight average molecular weight of the polymer is not limited, but preferably 500 to 5000000, and more preferably 1000 to 150000.

The polymer may be produced by, e.g., radical polymerization using publicly known method such as solution polymerization, bulk polymerization, emulsion polymerization and suspension polymerization. If necessary, the polymerization may be performed in a reaction system under the atmosphere of, or substituted by, inert gas such as nitrogen, carbon dioxide or helium. The polymerization temperature may be 0 to 100° C., and the polymerization time may be 10 minutes to 48 hours. Upon polymerization, polymerization initiator may be used. The examples of the polymerization initiator may include 2,2'-azobis (2-amidinopropane) dihydrochloride, 4,4'-azobis(4-cyanovaleric acid), 2,2'-azobis (2-(5-methyl-2-imidazoline-2-yl)propane) dihydrochloride, 2,2'-azobis (2-(2-imidazoline-2-yl) propane)dihydrochloride, 2,2'-azobisisobutylamide dihydrate, ammonium persulfate, potassium persulfate, benzoyl peroxide, diisopropyl peroxy dicarbonate, t-butylperoxy-2-ethylhexanoate, t-butyl peroxypivalate, t-butylperoxydiisobutylate, lauroyl peroxide, azobisisobutyronitrile (abbreviated hereinbelow as AIBN), 2,2'-azobis(2, 4-dimethylvaleronitrile), t-butyl peroxyneodecanoate (trade name "Perbutyl ND", manufactured by NOF Corporation, abbreviated hereinbelow as P-ND), or mixtures thereof. As the polymerization initiator, various redox type accelerators may be used. The polymerization initiator may be used in an amount of 0.01 to 5.0 parts by weight with respect to 100 parts by weight of the monomer composition.

Purification of the polymer may be performed in accordance with general purification methods such as reprecipitation, dialysis, and ultrafiltration.

The examples of the substances to be solubilized or emulsified by the present solubilizer or emulsifier may include, e.g., drugs such as indomethacin, shikonin, hydrocortisone, erythromycin, adriamycin, ethyl eicosapentaenoate (EPA-E), α-tocopherol, prostaglandins, bioactive peptides, vitamins, tetracycline, dexamethasone, diclofenamide, heleniene, calcium diiodostearate, and methazolamide; and oils and fats such as soybean oil, olive oil, safflower oil, sesame oil, hardened beaf tallow and hardened rapeseed oil.

The substance to be dispersed by the present dispersing agent may include, e.g., organic powders such as phthalocyanine, and inorganic powders such as carbon black and titanium oxide.

The present solubilizer, emulsifier and dispersing agent may further contain, in addition to the polymer as the effective ingredient, other solubilizers and various surfactants for solubilizing compounds and drugs, which are not much soluble in water, in a water-soluble solvent mainly containing water.

The present solubilizer, emulsifier or dispersing agent can solubilize, emulsify or disperse a larger amount of substance which is not much solublized, emulsified or dispersed in the prior art solution, emulsion or dispersion. Therefore, the present solubilizer, emulsifier and dispersing agent can be used in a wide variety of arts such as pharmaceuticals, compositions and coatings. Particularly, they are useful as a washing ingredient for shampoo, face washing agent, and detergents.

EXAMPLES OF THE INVENTION

The present invention will be described more in detail with reference to the Examples and Comparative Examples. However, the present invention is not limited thereto.

Example 1-1

MPC as the hydrophilic monomer (a) and butyl methacrylate (abbreviated hereinbelow as "BMA") as the hydrophobic monomer (b) were dissolved and mixed in ethanol so that the concentrations thereof were 0.473 mol/L and 1.10 mol/L, respectively. Nitrogen was blown into this solution for two hours. The temperature of the system was adjusted to 60° C. P-ND as the polymerization initiator was added to the solution so that the concentration thereof was 0.055 mol/L. Subsequently, the solution was stirred for three hours at 60° C. and then for one hour at 70° C., and cooled to room temperature. This solution was put in a dialysis membrane (manufactured by The Spectrum Companies, USA, trade name "Spectra/por.6. Mw CO.8000"), and dialysis operation was performed using ethanol:water=7:3 (V/V) of ten times the volume of the solution. The solvent was changed once a day. The dialysis was performed for seven days, to prepare a solution containing a polymer (referred to hereinbelow as "polymer A") that can be used as the effective ingredient of the solubilizer, emulsifier and dispersing agent. Measurement of the molecular weight, viscosity and content of MPC, as well as solubilizing, emulsifying and dispersing tests of the resulting polymer A were preformed as follows.

Molecular Weight Measurement (GPC)

The obtained solution containing the polymer A was dissolved in and diluted with chloroform:methanol=6:4 (V/V) containing 0.5 wt % lithium chloride, so that the concentration was adjusted to 3 wt %. The solution was filtered through a 0.5 µm membrane filter, to prepare a sample solution.

Analysis conditions for GPC were as follows. Eluent: chloroform:methanol=6:4 (V/V) containing 0.5 wt % lithium chloride. Elution rate: 1 ml/min. Amount of sample solution: 100 µl. Column temperature: 40°0 C. Columns: MIXED-C (two columns, manufactured by Polymer Laboratories, Ltd., UK). Detector: differential refractometer. Standard substance: polymethyl methacrylates (ten sorts of materials, the molecular weights of which were known to be in a range of $1.00 \times 10^3$ to $1.58 \times 10^6$). 100 µl of the sample solution was injected. Average molecular weight (Mw) and molecular weight distribution (Mw/Mn) was calculated with molecular weight calculation program (GPC program for SC-8020) installed in an integrator manufactured by TOSOH Co. The results are shown in Tables 1 and 2.

Viscosity Measurement

The obtained solution containing polymer A was diluted with ethanol:water=7:3 (V/V) so that the final concentration was adjusted to 10 wt % (the solution after purification by dialysis was directly diluted with the solvent, and the dry product was dissolved in the solvent). The resulting solution was left overnight. The viscosity of the solution was then measured with E type viscometer at rotations shown in Tables 1 and 2. The measurements were performed five times consequently, and average and deviation were calculated. The results are shown in Tables 1 and 2.

MPC Content Measurement (Composition Measurement (Phosphorus Quantification and Water Content Measurement))

Phosphorus quantification; the obtained solution containing the polymer A was air-dried, and dried in vacuo at 7020 C., to prepare a sample. 6 mg of the sample was dissolved in and diluted with distilled ethanol in 10 ml measuring flask, so that the volume was precisely adjusted to 10 ml. Exactly 50 µl of the solution was taken with microsyringe, and put into a washed tube. The solvent was removed at 100° C. with a block heater, and the residue was cooled to room temperature. To the tube, 0.25 ml of perchloric acid solution (70%) was added. The tube was capped with a glass ball. The sample was heated at 180° C. for 20 minutes to decompose the polymer using the block heater, and cooled to room temperature. 1.90 ml of distilled water, 0.40 ml of a 1.25% (wt/wt) ammonium molybdate aqueous solution and 0.40 ml of a 5% (wt/wt) ascorbic acid aqueous solution were added. The mixture was stirred with vortex mixer, and heated in boiling water bath for five minutes for coloring. Absorbance of the solution was measured at the wave length showing the maximum absorption (about 817.8 nm). Phosphorus content was quantified by a calibration curve separately generated using phosphoric acid.

Water content measurement; The obtained solution containing the polymer A was air-dried and dried in vacuo at 70° C., to prepare samples. Water content of the samples was measured by Karl Fischer's method.

From the results of water content measurement and the results of the phosphorus quantification, the composition of the polymer A after purification was evaluated, to calculate the content of MPC. The results are shown in Tables 1 and 2.

Solubilizing, Emulsifying and Dispersing Test 0.11 g of the obtained polymer A was dissolved in 1.2 g of water to prepare an aqueous sample solution. 0.1 g of activated charcoal powders were put on the back of a hand, and then shaken off the hand. The sample solution was put on the back of the hand having the activated charcoal adhered thereon. The back of the hand was rubbed for 10 seconds and then rinsed with flowing water. On the other hand, 0.1 g of activated charcoal powders were put on the back of another hand, and then shaken off the hand. The back of the hand was, without the sample solution, rubbed for 10 seconds and then rinsed with flowing water. The effect of the polymer A for washing off the activated charcoal adhered on the back of the hand and the moistness of the hand after drying was evaluated by these two tests. Further, similar tests were performed using 0.1 g of silicone oil instead of the activated charcoal powders. Further, similar tests were performed using 1.2 g of an aqueous solution containing 10 wt % polyoxyethylene (20 mol) sorbitan monooleate instead of the aqueous solution containing the polymer A. The results are shown in Table 3.

Examples 1-2 to 1-19

The monomer compositions shown in Tables 1 and 2 were polymerized in the same way as in Example 1-1 under conditions shown in Tables 1 and 2, and purified by one of the methods described below, to prepare solutions containing polymers which can be effective ingredients of solubilizers. Measurements and tests were performed in the same way as in Example 1-1 using the solution and polymers. The results are shown in Tables 1 to 3. EHMA in the tables refers to 2-ethylhexyl methacrylate. Purification Methods:

1) Dialysis was performed seven times with a dialysis membrane (manufactured by The Spectrum Companies, USA, trade name "Spectra/por.6. Mw CO.8000") against ethanol:water=7:3.
2) The polymer was reprecipitated from diethyl ether, dried, and then dialyzed seven times with the dialysis membrane (manufactured by The Spectrum Companies, USA, trade name "Spectra/por.6. Mw CO.8000") against ethanol:water=7:3. Further, reprecipitation from acetonitrile was performed two times.
3) Dialysis was performed seven times with the dialysis membrane (manufactured by The Spectrum Companies, USA, trade name "Spectra/por.6. Mw CO.8000") against ethanol:water=7:3. Further, reprecipitation from acetonitrile was performed two times.
4) The polymer was reprecipitated from diethyl ether, dried, and then dialyzed seven times with the dialysis membrane (manufactured by The Spectrum Companies, USA, trade name "Spectra/por.6. Mw CO.8000") against ethanol:water=7:3.
5) Reprecipitation from acetonitrile was performed two times.

TABLE 1

| | Examples | | | | | | | | | |
|---|---|---|---|---|---|---|---|---|---|---|
| | 1-1 | 1-2 | 1-3 | 1-4 | 1-5 | 1-6 | 1-7 | 1-8 | 1-9 | 1-10 |
| Hydrophobic monomer | BMA | BMA | BMA | BMA | BMA | BMA | BMA | BMA | BMA | BMA |
| Concentration upon polymerization (mol/l) | 1.10 | 1.17 | 1.22 | 1.25 | 1.37 | 1.10 | 1.10 | 1.10 | 1.10 | 1.49 |
| ratio (wt %) | 52.8 | 57.8 | 61.7 | 64.4 | 76.3 | 52.8 | 52.8 | 52.9 | 52.9 | 52.9 |
| Hydrophilic monomer | MPC | MPC | MPC | MPC | MPC | MPC | MPC | MPC | MPC | |
| Concentration upon polymerization (mol/l) | 0.473 | 0.411 | 0.363 | 0.332 | 0.205 | 0.474 | 0.474 | 0.474 | 0.474 | 0.639 |
| ratio (wt %) | 47.2 | 42.2 | 38.3 | 35.6 | 23.7 | 47.2 | 47.2 | 47.1 | 47.1 | 47.1 |
| Solvent for polymerization | ethanol | ethanol | ethanol | ethanol | ethanol | ethanol | ethanol | ethanol | ethanol | ethanol |
| Monomer concentration (wt %) | 33.9 | 33.4 | 32.6 | 32.1 | 30.0 | 34.4 | 34.4 | 34.4 | 34.4 | 45.0 |
| Polymerization initiator | P-ND | P-ND | P-ND | P-ND | P-ND | P-ND | P-ND | P-ND | P-ND | P-ND |
| Concentration (mol/l) | 0.055 | 0.055 | 0.055 | 0.055 | 0.055 | 0.0500 | 0.0508 | 0.0020 | 0.0020 | 0.0020 |
| Polymerization temperature (° C.) | 60  70 | 60  70 | 60  70 | 60  70 | 60  70 | *1 | 60  70 | 45 | 60  70 | 60  70 |
| Polymerization time (hours) | 3  1 | 3  1 | 3  1 | 3  1 | 3  1 | | 3  1 | 138.75 | 3  1 | 3  1 |
| Purification method | 1) | 1) | 1) | 1) | 1) | 1) | 1) | 1) | 2) | 2) |
| Characterization | | | | | | | | | | |
| Molecular weight (Mw) | 68000 | 68000 | 63000 | 60000 | 45000 | 66400 | 80600 | 208000 | 280000 | 429000 |
| Molecular weight distribution (Mw/Mn) | 1.45 | 1.61 | 1.51 | 1.43 | 1.45 | 1.51 | 1.77 | 1.55 | 1.55 | 1.86 |
| Viscosity measurement (rotation speed rpm) | 100 | 100 | 100 | 100 | 100 | 100 | 100 | 100 | 100 | 100 |
| Viscosity (mPa · s) | 8.2 | 6.9 | 6.7 | 6.5 | 5.9 | 7.7 | 8.3 | 21.2 | 34.2 | 80.2 |
| MPC content (mol %) | 28.5 | 19.0 | 17.5 | 15.8 | 10.5 | 27.1 | 24.6 | 22.5 | 23.7 | 26.8 |

*1 The temperature was elevated from 24° C. to 60° C. over 30 minutes, and reaction was carried at 60° C. for 2.5 hours and then at 70° C. for 1 hour.

TABLE 2

|  | Examples | | | | | | | | |
| --- | --- | --- | --- | --- | --- | --- | --- | --- | --- |
|  | 1-11 | 1-12 | 1-13 | 1-14 | 1-15 | 1-16 | 1-17 | 1-18 | 1-19 |
| Hydrophobic monomer | BMA | BMA | BMA | BMA | BMA | BMA | EHMA | BMA | — |
| Concentration upon polymerization (mol/l) | 2.07 | 2.50 | 0.224 | 0.459 | 1.03 | 1.49 | 0.917 | 0.75 | 0 |
| ratio (wt %) | 52.9 | 52.9 | 52.9 | 52.9 | 52.9 | 52.9 | 52.9 | 52.9 | 0 |
| Hydrophilic monomer | MPC | MPC | MPC | MPC | MPC | MPC | MPC | MPC |  |
| Concentration upon polymerization (mol/l) | 0.887 | 1.07 | 0.0958 | 0.197 | 0.441 | 0.639 | 0.393 | 1.13 | 0.450 |
| ratio (wt %) | 47.1 | 47.1 | 47.1 | 47.1 | 47.1 | 47.1 | 47.1 | 47.1 | 100 |
| Solvent for polymerization | ethanol | ethanol | ethanol | ethanol | ethanol | ethanol | ethanol | ethanol | ethanol |
| Monomer concentration (wt %) | 60.0 | 70.3 | 7.5 | 15.0 | 32.2 | 45.0 | 35.0 | 44.0 |  |
| Polymerization initiator | P-ND | P-ND | AIBN | AIBN | AIBN | AIBN | P-ND | AIBN | P-ND |
| Concentration (mol/l) | 0.002 | 0.002 | 0.002 | 0.002 | 0.002 | 0.002 | 0.05 | 0.0091 | 0.005 |
| Polymerization temperature (° C.) | 60 | 60 | 60  70 | 60  70 | 60 | 60 | 60  70 | 60 | 60 |
| Polymerization time (hours) | 2.25 | 0.367 | 3  1 | 3  1 | 18 | 18 | 3  1 | 15.5 | 6 |
| Purification method | 3) | 2) | 4) | 4) | 2) | 2) | 5) | 1) | 1) |
| Characterization |  |  |  |  |  |  |  |  |  |
| Molecular weight (Mw) | 635000 | 736000 | 66900 | 150000 | 190000 | 289000 | 49600 | 260000 | 106000 |
| Molecular weight distribution (Mw/Mn) | 2.01 | 2.01 | 1.40 | 1.40 | 1.81 | 2.02 | 1.51 | 5.18 | 2.05 |
| Viscosity measurement (rotation speed rpm) | 10 | 0.5 | 100 | 100 | 100 | 100 | — | — | — |
| Viscosity (mPa · s) | 1082 | 12662 | 7.9 | 16.0 | 27.2 | 42.8 | — | — | — |
| MPC content (mol. %) | 26.4 | 26.6 | 27.7 | 26.7 | 28.5 | 29.7 | 28.1 | 49.3 | 100 |

TABLE 3

|  | Substance to be washed off | Cleansing availability evaluation | Moistness evaluation |
| --- | --- | --- | --- |
| (1) | Activated charcoal | 20/20 | 19/20 |
| (2) | Activated charcoal | 2/20 | 0/20 |
| (3) | Activated charcoal | 20/20 | 2/20 |
| (1) | silicone oil | 17/20 | 19/20 |
| (2) | silicone oil | 0/20 | 0/20 |
| (3) | silicone oil | 19/20 | 1/20 |

(1): treated with aqueous solution containing the polymer A
(2): treated only with rubbing
(3): treated with surfactant Example 2-1

Solubilization with the Polymer A of Example 1-1

0.5 g of the polymer A prepared in Example 1-1 was dissolved in 1 g of ethanol. To the solution, 0.01 g of indomethacin was added and dissolved. The solution was then dialyzed with dialysis membrane (manufactured by The Spectrum Companies, USA, trade name "Spectra/por.6. Mw CO.8000") against 666 ml of purified water, which was exchanged 20 times. The dialyzed solution was then filtered through a membrane filter made of acetyl cellulose (0.45 μm). The state of the liquid was visually observed. The results are shown in Table 4.

Example 2-2

Solubilization with the Polymer A of Example 1-1

0.5 g of the polymer A prepared in Example 1-1 was dissolved in 1 g of water. To the solution, 0.01 g of shikonin was further added. The solution was irradiated with ultrasonic wave for 10 minutes using a probe-type ultrasonic irradiator (manufactured by The Spectrum Companies, USA, trade name "Astrason, XL2020, Heart Systems"). The resulting liquid was filtered through a membrane-filter made of acetyl cellulose (0.45 μm). The state of the liquid was visually observed. The results are shown in Table 4.

Examples 2-3 to 2-14

From compositions of the solubilizer, emulsifier or dispersing agent shown in Table 4 and substances to be solubilized, emulsified or dispersed that are drugs shown in Table 4, liquids were prepared in accordance with the method of Example 2-1 (dialysis) or the method of Example 2-2 (ultrasonic wave).

In Examples 2-5 and 2-6, in which additional solvents were mentioned in Table 4, the liquids were prepared by further mixing pyridine (Example 2-5) or toluene (Example 2-6) shown in Table 4 with the mixture, in addition to ethanol. In Example 2-5, filtration with the membrane filter was not performed. The state of the liquid was visually observed. The results are shown in Table 4.

TABLE 4

|  | Examples | | | | | | |
| --- | --- | --- | --- | --- | --- | --- | --- |
|  | 2-1 | 2-2 | 2-3 | 2-4 | 2-5 | 2-6 | 2-7 |
| Solubilizer, emulsifier, dispersing agent | Example 1-1 Polymer | Example 1-1 Polymer | Example 1-1 Polymer | Example 1-1 Polymer | Example 1-1 Polymer | Example 1-1 Polymer | Example 1-1 Polymer |

TABLE 4-continued

| Substance to be solubilized, emulsified or dispersed (g) | IDM 0.01 | SKN 0.01 | HC 0.01 | EM 0.01 | PC 0.01 | PR 0.01 | ADR 0.01 |
|---|---|---|---|---|---|---|---|
| Additional solvent Amount (g) | — | — | — | — | pyridine 0.5 | toluene 0.5 | — |
| Method for solubilizing emulsifying or dispersing | Dialysis | Ultrasonic wave | Ultrasonic wave | Dialysis | Dialysis | Dialysis | Dialysis |
| Result of visual observation of liquid | Light yellow homogenous solution | Black purple homogenous solution | Clear homogenous solution | Clear homogenous solution | Deep blue suspension | Clear homogenous solution | Orange homogenous solution |

| | Examples | | | | | | |
|---|---|---|---|---|---|---|---|
| | 2-8 | 2-9 | 2-10 | 2-11 | 2-12 | 2-13 | 2-14 |
| Solubilizer, emulsifier, dispersing agent | Example 1-1 Polymer | Example 1-1 Polymer | Example 1-1 Polymer | Example 1-17 Polymer | Example 1-17 Polymer | Example 1-17 Polymer | Example 1-19 Polymer |
| Substance to be solubilized, emulsified dispersed (g) | TP 0.1 | OO 0.01 | SO 0.01 | IDM 0.01 | SKN 0.01 | EPA 0.1 | SKN 0.01 |
| Additional solvent Amount (g) | — | — | — | — | — | — | — |
| Method for solubilizing emulsifying or dispersing | Ultrasonic wave | Ultrasonic wave | Ultrasonic wave | Dialysis | Dialysis | Ultrasonic wave | Dialysis |
| Result of visual observation of liquid | Clear homogenous solution | Milky white homogenous emulsion | Milky white homogenous emulsion | Light yellow homogenous solution | Blackish purple homogenous solution | Pale milky white homogenous emulsion | Blue black homogenous solution |

IDN: indomethacin, SKN: shikonin, HC; hydrocortisone, PR: pyrene, EM: erythromycin, PC: phthalocyanine, ADR: adriamycin, TP: α-tocopherol, OO: olive oil, SO: soybean oil, EPA: ethyl eicosapentanoate From the results in Table 4, it is found that the solubilizer, emulsifier and dispersing agent of the present invention have an excellent solubilizing, emulsifying and dispersing ability, respectively.

Example 3-1

Using the aqueous solution of the polymer A prepared in Example 1-1 (concentration; 10 g/liter) as a detergent solution, a washing test with a washing test machine (Terg-O-tometer; manufactured by K. K. Ueshima Seisakusyo) was performed in accordance with the following procedure. The results are shown in Table 5.
<Washing Test>
In the washing tub of the washing tester, the washing liquid prepared at the aforementioned concentration wasplaced. Subsequently, two sheets of artificially dirtied cloth, which will be described later, and two sheets of untreated cotton cloth (10×10 cm) for redeposition test were put in the tub, and washed at 150 rpm for 30 minutes at washing liquid temperature of 40° C., with one rotation reverse per 30 seconds. Subsequently, the test cloth sheets were taken out of the washing liquid, and rinsed for 5 minutes in hot water at 40° C. at 150 rpm with one rotation reverse per 30 seconds. The rinsing was performed twocycles. The test cloth sheets were then dried to make sample cloths for measurement.

As to four sorts of cloth, i.e., the washed cloth and washed cloth for redeposition test that have been subjected to the above washing test, as well as artificially dirtied cloth which will be described later, and untreated cotton cloth for redeposition test (untreated cloth), reflectance at four points on each sheet was measured by a color computer (manufactured by Suga Shikenki K. K.). The reflectance (%) of the dirtied cloths or untreated cloth was calculated by the following equation. The reflectances at the four points on each cloth sheet were averaged. The results are shown in Table 6.
Washing ratio (%)=(((reflectance of the washed dirtied cloth)—(reflectance of the dirtied cloth))/((reflectance of the untreated cloth)—(reflectance of the dirtied cloth)))×100
Redeposition ratio (%)=(((reflectance of the untreated cloth)—(reflectance of the washed cloth for redeposition test))/((reflectance of the untreated cloth)-(reflectance of the dirtied cloth)))×100.
<Preparation of Dirtied Cloth with Artificial Dirt>
In a dispersion of artificial dirt consisting of 1.5 g of oleic acid, 0.75 g of palmitic acid, 0.75 g of myristic acid, 3.0 g of hardened rapeseed oil, 1.0 g of cholesterol, 0.5 g of squalane, 1.0 g of cetyl alcohol, 1.5 g of liquid paraffin, 1.75 g of activated charcoal and 800 ml of 1,1,1-trichloroethylene, two sheets of cotton cloth (10×10 cm) were put. After one minute of immersion, cloth sheets were taken out, and squeezed between rollers to adjust the pressed ratio to 100%. The cloths were then dried to prepare the dirtied cloths.

Comparative Example 1

The washing test was performed in the same way as in Example 3-1 except that one liter of purified water not containing the polymer A prepared in Example 1-1 was used as the washing liquid.

The results are shown in Table 5.

TABLE 5

|  | Example 3-1 | Comparative Example 1 |
|---|---|---|
| Washing ratio | 34.9% | 3.1% |
| Redeposition ratio | 1.3% | not measured |

From the results of Example 3-1 and Comparative Example 1, it is found that the washing agent containing the solubilizer, emulsifier and dispersing agent of the present invention has high washing ratio. It is also found that the Example 3-1 resulted in low redeposition ratio.

Examples 4-1 to 4-3

Shampoo compositions described in Table 6 were prepared and the properties thereof were evaluated in accordance with the following evaluation procedure. The results are shown in Table 6.

<Evaluation of Creaming of the Foam>

Twenty women (20 to 60 years old), as panels, washed their hair using 5 ml each of the shampoo compositions, for evaluating creaming of the foam of the shampoo compositions. Evaluation was made in accordance with the following: 2 points for creamy feeling of the foam; 1 point for slight creamy feeling; and 0 point for no creamy feeling but loose feeling. Average point was calculated. Compositions resulting in 1.5 or more points in average were evaluated as good compositions for foaming property.

<Evaluation of the Feel of Smoothness at the Time of Shampooing Hair with Fingers>

Twenty women (20 to 60 years old), as panels, washed their hair using 5 ml each of the shampoo compositions, for evaluating the feel of smoothness of their hair during shampooing with their fingers. Evaluation was made in accordance with the following: 2 points for smooth feeling on fingers and no hair tangling; 1 point for smooth feeling on fingers but with slight hair tangling; and 0 point for very poor smoothness on finger with hair tangling. Average point was calculated. Compositions resulting in 1.5 or more points in average were evaluated as giving good smoothness of hair during shampooing.

<Evaluation of the Feel of Smoothness at the Time of Combing Hair After Shampooing>

Twenty women (20 to 60 years old), as panels, washed their hair using 5 ml each of the shampoo compositions, dried their hair, and evaluated the feel of smoothness in combing. Evaluation was made in accordance with the following: 2 points for smooth combing; 1 point for slight tangling of hair with the comb; and 0 point for very poor smoothness in combing. Average point was calculated. Compositions resulting in 1.5 or more points in average were evaluated as giving good smoothness in combing.

<Evaluation of Conditioning Efficacy after Shampooing>

Twenty women (20 to 60 years old), as panels, washed their hair using 5 ml each of the shampoo compositions, dried their hair, and evaluated conditioning efficacy. Evaluation was made in accordance with the following: 2 points for excellent conditioning efficacy; 1 point for slight conditioning efficacy; and 0 point for no conditioning efficacy. Average point was calculated. Compositions resulting in 1.5 or more points in average were evaluated as having good conditioning effect.

<Evaluation of Hair Settability after Shampooing and Drying>

Twenty women (20 to 60 years old), as panels, washed their hair using 5 ml each of the shampoo compositions, dried their hair, and evaluated hair settability. Evaluation was made in accordance with the following: 2 points for excellent settability; 1 point for slight settability; and 0 point for poor settability. Average point was calculated. Compositions resulting in 1.5 or more points in average were evaluated as giving good hair setting effect.

<Evaluation of Moistness of Hair after Shampooing and Drying>

Twenty women (20 to 60 years old), as panels, washed their hair using 5 ml each of the shampoo compositions, dried their hair, and evaluated moistness of hair. Evaluation was made in accordance with the following: 2 points for excellent moistness feeling; 1 point for slightly moistness feeling; and 0 point for no moistness feeling. Average point was calculated. Compositions resulting in 1.5 or more points in average were evaluated as giving good moistness feeling to hair.

<Stability of the Composition with the Lapse of Time>

Shampoo compositions described in Table 6 were sterilized by filtration, and stored at −5° C., 25° C. or 45° C. for one month. Visual observation of the composition was then performed and evaluated in three levels of ○, Δ and X. ○: the composition had good stability, and clearness or trace of turbidity was observed. Δ: the composition had slightly poor stability, and slight turbidity or coloring was observed. X: the composition had poor stability, and precipitation and significant coloring were observed.

Comparative Example 2

Evaluation was made in the same way as in Examples 4-1 to 4-3 except that the shampoo composition described in Table 6 was employed. The results are shown in Table 7.

TABLE 6

|  | Examples | | | Comp. |
|---|---|---|---|---|
|  | 4-1 | 4-2 | 4-3 | Ex. 2 |
| Polymer of Example 1-1 | 25 | 0 | 0 | 0 |
| Polymer of Example 1-17 | 0 | 25 | 0 | 0 |
| Polymer of Example 1-19 | 0 | 0 | 25 | 0 |
| Lauric acid triethanolamine salt | 0 | 0 | 0 | 6 |
| Myristic acid triethanolamine salt | 0 | 0 | 0 | 3 |
| Palmitic acid triethanolamine salt | 0 | 0 | 0 | 1 |
| Oleic acid triethanolamine salt | 0 | 0 | 0 | 2 |
| Polyoxyethylene (3 mol) lauryl ether sulfuric acid triethanol amine salt | 0 | 0 | 0 | 2 |
| N-cocoyl-N-methyltaurine sodium salt | 0 | 0 | 0 | 2 |
| Lauryliminodiacetate sodium salt | 0 | 0 | 0 | 1 |
| N-cocoyl-N'-carboxymethyl-N'-(2-hydroxyethyl)ethylenediamine | 0 | 0 | 0 | 2 |
| Cocoamid propyl dimethyl amino acetate betain | 0 | 0 | 0 | 1 |
| N,N-bis(hydroxyethyl)lauryl amide | 0 | 0 | 0 | 2 |
| Stearyltrimethylammonium chloride | 0 | 0 | 0 | 0.5 |
| Distearyldimethylammonium chloride | 0 | 0 | 0 | 0.5 |
| Purified water | rest | rest | rest | rest |

TABLE 6-continued

|  | Examples | | | Comp. |
| --- | --- | --- | --- | --- |
|  | 4-1 | 4-2 | 4-3 | Ex. 2 |
| Evaluation measurement | | | | |
| Creaming of foam | 0.5 | 0.7 | 0.7 | 1.6 |
| Feel of smoothness at the time of shampooing with fingers | 1.7 | 1.8 | 1.6 | 0.6 |
| Feel of smoothness at the time of combing hair after shampooing | 1.9 | 1.8 | 1.9 | 0.8 |
| Conditioning efficacy after shampooing | 1.9 | 1.8 | 1.8 | 1.0 |
| Settability after drying | 1.9 | 1.8 | 1.9 | 1.8 |
| Moistness after drying | 2.0 | 1.9 | 1.9 | 0.8 |
| Stability with the lapse of time | ○ | ○ | ○ | ○ |

From the results in Table 6, it is found that the solubilizer, emulsifier and dispersing agent of the present invention resulted in excellent smoothness at the time of shampooing hair, excellent smoothness at the time of combing hair, excellent conditioning efficacy, excellent hair settability, and excellent moistness. It is also found that the compositions have good stability with the lapse of time.

Examples 5-1 to 5-3

Face washing compositions described in Table 7 were prepared and the properties thereof were evaluated in accordance with the following evaluation procedure. The results are shown in Table 7.

<Evaluation of Creaming of the Foam>

Twenty women (20 to 60 years old), as panels, washed their faces using 5 ml each of the face washing compositions, for evaluating creaming of the foam. Evaluation was made in accordance with the following: 2 points for excellent creaming of the foam; 1 point for slightly creamy feeling; and 0 point for no creamy feeling but rough feeling. Average point was calculated. Compositions resulting in 1.5 or more points in average were evaluated as good composition for foaming property.

<Evaluation of Stickiness after Rinsing>

Twenty women (20 to 60 years old), as panels, washed their faces using 5 ml each of the face washing compositions and then rinsed their faces three times using 1 liter each of hot water at about 40° C. with rubbing, for evaluating stickiness. Evaluation was made in accordance with the following: 4 points for no stickiness; 3 points for trace of stickiness; 2 points for slight stickiness; and 1 point for significant stickiness. Average point was calculated. Compositions resulting in 3.0 or more points in average were evaluated as giving no stickiness.

<Evaluation of Refreshing Feeling after Rinsing>

Twenty women (20 to 60 years old), as panels, washed their faces using 5 ml each of the face washing compositions and then rinsed their faces three times using 1 liter each of hot water at about 40° C. with rubbing, for evaluating refreshing feeling. Evaluation was made in accordance with the following: 4 points for refreshing feeling; 3 points for slightly refreshing feeling; 2 points for trace of refreshing feeling; and 1 point for no refreshing feeling. Average point was calculated. Compositions resulting in 3.0 or more points in average were evaluated as giving good refreshing feeling.

<Evaluation of Moistness of Skin After Face Washing and Drying>

Twenty women (20 to 60 years old), as panels, washed their faces using 5 ml each of the face washing compositions, rinsed, and then evaluated moistness of the skin. Evaluation was made in accordance with the following: 2 points for excellent moistness of skin; 1 point for slightly moistness of skin; and 0 point for little moistness of skin. Average point was calculated. Compositions resulting in 1.5 or more points in average were evaluated as giving good moistness of skin.

<Stability of the Composition with the Lapse of Time>

Evaluations were made in the same way as in evaluation of stability with the lapse of time of the shampoo compositions in Examples 4-1 to 4-3.

Comparative Example 3

Evaluations were made in the same way as in Examples 5-1 to 5-3, except that a face washing composition described in Table 7 was employed. The results are shown in Table 7.

TABLE 6

|  | Examples | | | Comp. |
| --- | --- | --- | --- | --- |
|  | 5-1 | 5-2 | 5-3 | Ex. 3 |
| Polymer of Example 1-1 | 25 | 0 | 0 | 0 |
| Polymer of Example 1-17 | 0 | 25 | 0 | 0 |
| Polymer of Example 1-19 | 0 | 0 | 25 | 0 |
| Potassium laurate | 0 | 0 | 0 | 6 |
| Potassium myristate | 0 | 0 | 0 | 3 |
| Potassium palmitate | 0 | 0 | 0 | 1 |
| Potassium oleate | 0 | 0 | 0 | 2 |
| N-cocoyl-N-methyltaurine sodium salt | 0 | 0 | 0 | 2 |
| Polyoxyethylene (3 mol) coconut oil fatty acid amide ether sulfate sodium salt | 0 | 0 | 0 | 2 |
| Sodium lauryliminodiacetate | 0 | 0 | 0 | 1 |
| N-cocoyl-N'-carboxymethyl-N'-(2-hydroxyethyl)ethylenediamine | 0 | 0 | 0 | 2 |
| Cocoamido propyl dimethyl amino acetate betaine | 0 | 0 | 0 | 1 |
| N,N-bis(hydroxyethyl)lauryl amide | 0 | 0 | 0 | 2 |
| Purified water | rest | rest | rest | rest |
| Evaluation measurement | | | | |
| Creaming of foam | 0.5 | 0.4 | 0.7 | 1.6 |
| Stickiness after rinsing | 3.4 | 3.6 | 3.6 | 1.2 |
| Refreshing feeling after rinsing | 3.8 | 3.6 | 3.8 | 1.6 |
| Moistness after rinsing | 2.0 | 1.9 | 1.9 | 0.8 |
| Stability with the lapse of time | ○ | ○ | ○ | ○ |

From the results in Table 7, it is found that the solubilizer, emulsifier and dispersing agent of the present invention resulted no stickiness, excellent refreshing feeling, and excellent moistness. It is also found that the composition has good stability with the lapse of time.

Referential Example 1
(Measurement of Critical Micelle Concentration)

Aqueous solutions containing various concentrations in a range of 0.255 to 255 mg/liter of the polymer A prepared in Example 1—1 were prepared. Each solution was mixed with an equal amount of aqueous solution containing $6.0 \times 10^{-7}$ mol/liter of pyrene. Fluorescence intensity of these solutions was measured at Em=350 to 400 nm under the conditions of Ex=384 nm. From peak 1 (P-1) within 372 to 376 nm and peak 3 (P-3) within 383 to 385 nm, peak ratio ((P-1)/(P-3)) was calculated, and plotted with respect to the concentration of the polymer A of Example 1—1. The results are shown in FIG. 1.

In FIG. 1, numerals along the axis of ordinates refer to the value of the peak ratio ((P-1)/(P-3)), and numerals along the axis of abscissas refer to the concentration of the polymer A (mg/l).

The peak ratio ((P-1) / (P-3)) of the fluorescence intensity of pyrene is known to be about 1.8 under hydrophilic condition and lower than 1.8 under hydrophobic condition. From the results in FIG. 1, it is found that the aqueous solution of the polymer A of Example 1—1 has an end point of curve at concentration of about 3 mg/liter, and has peak ratio ((P-1) /(P-3)) of <1.8 at higher concentration. Namely, the polymer A of Example 1—1 forms micelle at the concentration of about 3 mg/liter or more, and the polymer has a surfactant property which can be utilized as a solubilizer, emulsifier or dispersing agent.

Referential Example 2
(Tests for Biological Safety)
Back Mutation Test Using Bacteria Using the polymer A prepared in Example 1-1 as a sample, tests were performed in accordance with back mutation test method of Yakumukyoku Yakushin 1 No.24 (Sep. 11, 1989), Ministry of Health and Welfare of Japan. That is, back mutation test including metabolic activation with Escherichia coli WP2 uvr A strain and four sorts of bacteria of Salmonellatyphimurium TA strain were performed for the polymer A prepared in Example 1-1 at a concentration of 156 to 5000 µg/plate. As a result, there was no recognition of increasing in the number of the back mutation colony in any of the experiments. From the above, it is concluded that the polymer A has negative mutagenesis.

Colony Formation Inhibition Test with Cultured Cells

Using the polymer A prepared in Example 1-1 as a sample, colony formation inhibition test was performed in accordance with "Guideline for basic biological tests for medical devices and medical materials" (Yakuki No.99, Betten, 1995). That is, the sample was prepared so that the concentration of the polymer A prepared in Example 1-1 was 0.5 to 2 mg/ml in M05 medium, and the number of colonies having 50 cells or more was counted, using 21st generation of Chinese hamster fibroblast cell V79 strain. As a result, no particular lowering of colony formation ratio in the sample or negative control test liquid was found, with respect to the untreated test liquid. Therefore, it is concluded that the sample containing the polymer A has negative colony formation inhibition.

Pyrogen Test

Using the polymer A prepared in Example 1-1 as a sample, pyrogen test was performed in accordance with general test methods of Japanese Pharmacopoeia 12th edition. That is, a physiological saline solution containing 56µg/ml of the polymer A prepared in Example 1-1, as the sample, was administered to male Japanese white rabbit in an amount of 10 ml per 1 kg body weight via an auricular vein. The body temperature was then measured three times with one-hour intervals. The measurements were compared to the control temperature. As a result, there were no rabbits showing rise of body temperature of 0.6° C. or more with respect to the control body temperature. From these results, it is concluded that the polymer A is negative as to the pyrogen test.

Intradermal Test

Using the polymer A prepared in Example 1-1 as a sample, intradermal test was performed in accordance with general test methods of Japanese Pharmacopoeia 12th edition. That is, 0.2 ml each of a physiological saline solution containing 64 µg/ml of the polymer A prepared in Example 1-1, as the sample, was administered intradermally at ten points in one side of backbone of a male Japanese white rabbit. The portion received the sample was observed 24 hours, 48 hours and 72 hours after the administration. As a result, no topical changing such as erythema, edema, bleeding or necrosis was recognized. From the above, it is concluded that the intradermal test for polymer A is negative.

Acute Toxicity Test

Using the polymer A prepared in Example 1-1 as a sample, acute toxicity test was performed in accordance with general test methods of Japanese Pharmacopoeia 12th edition. That is, a physiological saline solution containing 56 µg/ml of the polymer A prepared in Example 1-1, as the sample, was administered one time to a male ddy mouse in an amount of 50 ml per 1 kg body weight of the mouse via tail vein. After the administration, the mouse was observed for five days. No abnormality or death of mouse was recognized. From this result, it is concluded that the acute toxicity test for the sample is negative.

Hemolysis Test

Using the polymer A prepared in Example 1-1 as a sample, hemolysis test was performed in accordance with general test methods of Japanese Pharmacopoeia 12th edition. That is, 10 ml of a physiological saline solution containing 5 µg/ml of the polymer A prepared in Example 1-1 was admixed with 0.1 ml of defibrinized blood made from the blood taken from a male Japanese white rabbit. The mixture was left at 37° C. for 24 hours, and the extent of hemolysis was examined visually. As a result, no hemolysis was recognized. Thus, it is concluded that the hemolysis test for the polymer A is negative.

Acute Toxicity Test (Intravenous Administration)

Using the polymer prepared in Example 1-18 as a sample, acute toxicity test (intravenous administration) was performed on mouse. That is, single dose of the polymer prepared on Example 1-18 was intravenously administered in an amount of 200 mg/kg each to male and female mice. No abnormality or death of the test animals was recognized. Thus, the lethal dose of single intravenous administration to the subject mouse, both male and female, is recognized to be more than 200 mg/kg.

Skin Sensitization Test

Using the polymer prepared in Example 1-6 as a sample, skin sensitization test was performed in accordance with Maximization method on a guinea pig. That is, the skin of the guinea pig was previously sensitized by intradermal injection and close application. On the skin, an ethanol solution containing 5%, 0.5% or 0.05% of the polymer prepared in Example 1-6 was applied. After 24 hours, 48 hours and 72 hours, the skin reaction of the applied portion was scored in accordance with the evaluation standard of Draize method, to calculate sensitization positive ratio in each observation. As a result, the sensitization positive ratio was 0% for any observation time and concentration. From the above, the sample is recognized to have no dermal sensitization ability.

Dermal Primary Stimulation Test

Using the polymer prepared in Example 1-18 as a sample, dermal primary stimulation test was performed. That is, hair on the backs of six healthy white rabbits (12 to 16 weeks old, body weight of 2.50 to 3.11 kg) was shaved. On the shaved portion, a gauze in a size of 2.5×2.5 cm was applied, on which 0.5 ml of the solution (40% aqueous solution) of the polymer prepared in Example 1-18 was dropped. The rabbits were fixed in corsets. After 1 hour, 24 hours, 48 hours and 72 hours, formation of erythema and edema was evaluated. As a result, the average evaluation was 0.0. It is thus recognized that the sample is a non-stimulatory substance.

Acute Toxicity (Oral Administration)

Using the polymer prepared in Example 1-18 as a sample, acute toxicity test on mouse (oral administration) was performed. That is, single dose each of 5000 mg/kg of the polymer prepared in Example 1-18 was orally administered to male and female mice which had been fasted. During 14 days of observation period, no abnormality or death of the test animals were recognized. Thus, the lethal dose of single oral administration of the sample to the mice, both male and female, is considered to be more than 5000 mg/kg.

From the results of the above tests, it is found that the polymer, which is the effective ingredient of the solubilizer, emulsifier and dispersing agent of the present invention, has high biological safety.

What is claimed is:

1. A solubilizer comprising as an effective ingredient a polymer produced by polymerizing a monomer composition containing a hydrophilic monomer (a) having in a side chain thereof a group represented by the formula (1):

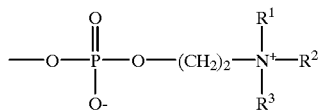
(1)

wherein $R^1$, $R^2$ and $R^3$ denote a hydrogen atom or an alkyl group having 1 to 4 carbon atoms, and are the same or different groups, said polymer being soluble in a solvent containing water.

2. The solubilizer of claim 1 wherein said hydrophilic monomer (a) is 2-(methacryloyloxy)ethyl-2'-(alkyl-substituted or non-substituted ammonio)ethyl phosphate represented by the formula (2):

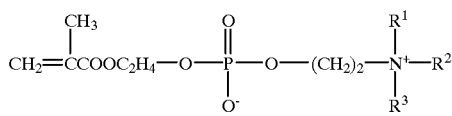
(2)

wherein $R^1$, $R^2$ and $R^3$ denote a hydrogen atom or an alkyl group having 1 to 4 carbon atoms, and are the same or different groups.

3. A solubilizer comprising as an effective ingredient a polymer produced by polymerizing a monomer composition consisting of, as a hydrophilic monomer (a), 100 to 20 wt % of 2-(methacryloyloxy)ethyl-2-(alkyl-substituted or non-substituted ammonio)ethyl phosphate represented by the formula (2):

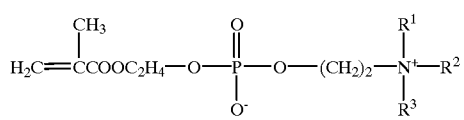
(2)

(wherein $R^1$, $R^2$ and $R^3$ denote a hydrogen atom or an alklyl group having 1 to 4 carbon atoms, and are the same or different groups) and, as a hydrophobic monomer (b), 0 to 80 wt % of (meth)acrylate represented by the formula (3):

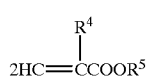
(3)

(wherein $R^4$ denotes a hydrogen atom or a methyl group, and $R^5$ denotes an alkyl group having 4 to 8 carbon atoms), said polymer being soluble in a solvent containing water.

4. An emulsifier comprising as an effective ingredient a polymer produced by polymerizing a monomer composition containing a hydrophilic monomer (a) having in a side chain thereof a group represented by the formula (1):

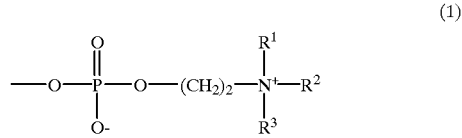
(1)

wherein $R^1$, $R^2$ and $R^3$ denote a hydrogen atom or an alkyl group having 1 to 4 carbon atoms, and are the same or different groups, said polymer being soluble in a solvent containing water.

5. The emulsifier of claim 4 wherein said hydrophilic monomer (a) is 2-(methacryloyloxy)ethyl-2'-(alkyl-substituted or non-substituted ammonio)ethyl phosphate represented by the formula (2):

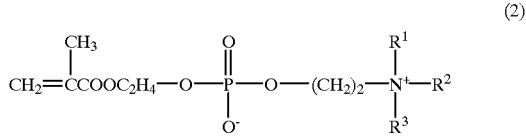
(2)

wherein $R^1$, $R^2$ and $R^3$ denote a hydrogen atom or an alkyl group having 1 to 4 carbon atoms, and are the same or different groups.

6. An emulsifier comprising as an effective ingredient a polymer produced by polymerizing a monomer composition consisting of, as a hydrophilic monomer (a), 100 to 20 wt % of 2-(methacryloyloxy)ethyl-2'-(alkyl-substituted or non-substituted ammonio)ethyl phosphate represented by the formula (2):

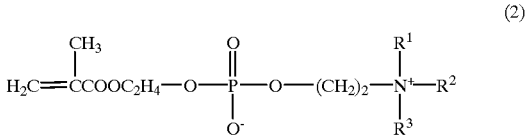
(2)

(wherein $R^1$, $R^2$ and $R^3$ denote a hydrogen atom or an alkyl group having 1 to 4 carbon atoms, and are the same or different groups) and, as a hydrophobic monomer (b), 0 to 80 wt % of (meth) acrylate represented by the formula (3):

(3)

(wherein $R^4$ denotes a hydrogen atom or a methyl group, and $R^5$ denotes an alkyl group having 4 to 8 carbon atoms), said polymer being soluble in a solvent containing water.

7. A dispersing agent comprising as an effective ingredient a polymer produced by polymerizing a monomer composition containing a hydrophilic monomer (a) having in a side chain thereof a group represented by the formula (1):

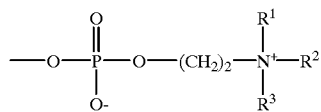
(1)

wherein $R^1$, $R^2$ and $R^3$ denote a hydrogen atom or an alkyl group having 1 to 4 carbon atoms, and are the same or different groups, said polymer being soluble in a solvent containing water.

8. The dispersing agent of claim 7 wherein said hydrophilic monomer (a) is 2-(methacryloyloxy)ethyl-2'-(alkyl-substituted or non-substituted ammonio)ethyl phosphate represented by the formula (2):

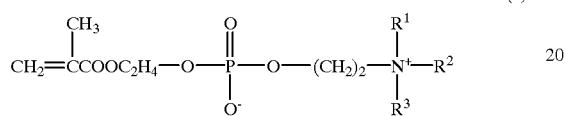
(2)

wherein $R^1$, $R^2$ and $R^3$ denote a hydrogen atom or an alkyl group having 1 to 4 carbon atoms, and are the same or different groups.

9. A dispersing agent comprising as an effective ingredient a polymer produced by polymerizing a monomer composition consisting of, as a hydrophilic monomer (a) 11 to 20 wt % of 2-(methacryloyloxy)ethyl-2'-(alkyl-substituted or non-substituted ammonio)ethyl phosphate represented by the formula (2):

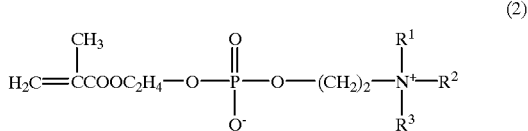
(2)

(wherein $R^1$, $R^2$ and $R^3$ denote a hydrogen atom or an alkyl group having 1 to 4 carbon atoms, and are the same or different groups) and, as a hydrophobic monomer (b) 0 to 80 wt % of (meth)acrylate represented by the formula (3):

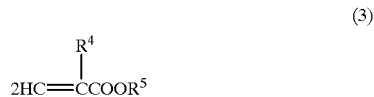
(3)

(wherein $R^4$ denotes a hydrogen atom or a methyl group, and $R^5$ denotes an alkyl group having 4 to 8 carbon atoms), said polymer being soluble in a solvent containing water.

* * * * *

UNITED STATES PATENT AND TRADEMARK OFFICE
CERTIFICATE OF CORRECTION

PATENT NO.    : 6,214,957 B1
DATED         : April 10, 2001
INVENTOR(S)   : Daijiro Shiino et al.

It is certified that error appears in the above-identified patent and that said Letters Patent is hereby corrected as shown below:

<u>Title page,</u>
Item [73], Assignee, change "Japan Science Technology" to -- Japan Science and Technology --.

Signed and Sealed this

Twenty-ninth Day of April, 2003

JAMES E. ROGAN
*Director of the United States Patent and Trademark Office*